US005695963A

United States Patent [19]
McKnight et al.

[11] Patent Number: 5,695,963
[45] Date of Patent: Dec. 9, 1997

[54] ENDOTHELIAL PAS DOMAIN PROTEIN

[75] Inventors: Steven L. McKnight; David W. Russell; Hui Tian, all of Dallas, Tex.

[73] Assignee: Board of Regents, The University of Texas System, Austin, Tex.

[21] Appl. No.: 785,241

[22] Filed: Jan. 17, 1997

[51] Int. Cl.$^6$ .......................... C12P 21/00; C07H 21/04; C07K 14/47; G01N 33/53

[52] U.S. Cl. .......................... 435/69.1; 435/7.1; 435/243; 435/325; 530/350; 536/23.5; 536/24.31

[58] Field of Search ...................... 435/7.1, 69.1, 435/243, 325; 536/23.5, 24.31; 530/350

*Primary Examiner*—James Ketter
*Assistant Examiner*—Robert Schwartzman
*Attorney, Agent, or Firm*—Richard Aron Osman

[57] ABSTRACT

The invention provides methods and compositions relating to endothelial PAS domain protein 1 (EPAS1) and related nucleic acids. The proteins may be produced recombinantly from transformed host cells from the disclosed EPAS1 encoding nucleic acids or purified from human cells. The invention provides isolated EPAS1 hybridization probes and primers capable of specifically hybridizing with the disclosed EPAS1 gene, EPAS1-specific binding agents such as specific antibodies, and methods of making and using the subject compositions in diagnosis, therapy and in the biopharmaceutical industry.

11 Claims, No Drawings

ENDOTHELIAL PAS DOMAIN PROTEIN

The research carded out in the subject application was supported in part by grants from the National Institutes of Health. The government may have rights in any patent issuing on this application.

INTRODUCTION

1. Field of the Invention

The field of this invention is transcription factor proteins involved in vascularization.

2. Background

Roughly a dozen proteins classified as basic helix-loop-helix/PAS domain transcription factors have been described in both vertebrates and invertebrates. Members of this class derive their name from the shared presence of a basic helix-loop-helix (bHLH) motif that specifies sequence dependent recognition of DNA and a PAS domain composed of two imperfect repeats. PAS is an acronym derived from the first three proteins observed to contain this motif. These include the product of the period gene of *Drosophila melanogaster* (Jackson et al. 1986; Citri et al. 1987), the aryl hydrocarbon nuclear transporter gene (ARNT) of mammals (Burbach et al. 1992), and the product of the fruit fly single-minded gene (Nambu et al. 1991).

The imperfect, direct repeats within the PAS domain are approximately 50 amino acids in length and contain a signature His-X-X-Asp sequence in each repeal. Three biochemical functions have been assigned to the PAS domain. First, it acts in concert with the helix-loop-helix domain of bHLH/PAS proteins to form a dimerization surface (Reisz-Porszasz et al. 1994; Fukunaga et al. 1995; Lindebro et al. 1995). In the case of the period gene product, which lacks a bHLH domain, the PAS domain specifies heterodimerization with the product of the timeless locus (Gekakis et al. 1995i Myers et al. 1995). Interaction between the period and timeless gene products represents a crucial event in the control of circadian rhythm in fruit flies (Hunter-Ensor et al. 1996; Lee et al. 1996; Myers et al. 1996; Zeng et al 1996). In contrast, the aryl hydrocarbon receptor (AHR) heterodimerizes with ARNT via PAS domain interactions (Fukunaga et al. 1995), producing a heterodimer that is competent for nuclear gene interaction. Second, the PAS domain mediates interaction with heat shock protein 90 (HSP-90). Several PAS domain proteins, including the single-minded gene product and the AHR, can be sequestered in the cytoplasm in an inactive state. Maintenance of the inactive state involves interactions between the PAS domain and HSP-90 (Perdew, 1988; Chen and Perdew, 1994; Henry and Gasiewicz, 1993; McGuire et al. 1995). Finally, the PAS domain of the AHR facilitates high affinity binding of certain xenobiotic compounds including dioxin (reviewed in Hankinson, 1995; Schmidt and Bradfield, 1996).

PAS domain transcription factors perform diverse functions in a variety of cell types and organisms. The period gene product helps regulate circadian rhythm in fruit flies (Konopka and Benzer, 1971), whereas the mammalian AHR provides response to xenobiotics by activating genes whose products facilitate detoxification (Schmidt and Brad field, 1996). A more recently described member of the PAS domain family, hypoxia inducible factor (HIF-1α), activates genes whose products regulate hematopoiesis in response to oxygen deprivation (Wang et al. 1995). In Drosophila, the single-minded gene product affects neurogenesis (Nambu et al. 1991) and the trachealess gene product controls the formation of tubular structures in the embryo (Wilk et al. 1996; Isaac and Andrew, 1996).

The utilization of bHLH/PAS domain proteins in diverse species and physiological processes raises the possibility that this family of transcription factors might consist of many undiscovered members. Here we report the initial characterization of new members of this protein family collectively designated endothelial PAS domain protein 1 (EPAS1).

SUMMARY OF THE INVENTION

The invention provides methods and compositions relating to endothelial PAS domain protein 1 (EPAS1), related nucleic acids, and protein domains thereof having EPAS1-specific activity. EPAS1 proteins can regulate specification of endothelial tissue, such as vasculature, the blood brain barrier, etc. The proteins may be produced recombinantly from transformed host cells from the subject EPAS1 encoding nucleic acids or purified from mammalian cells. The invention provides isolated EPAS1 hybridization probes and primers capable of specifically hybridizing with the disclosed EPAS1 gene, EPAS1-specific binding agents such as specific antibodies, and methods of making and using the subject compositions in diagnosis (e.g. genetic hybridization screens for EPAS1 transcripts), therapy (e.g. gene therapy to modulate EPAS1 gene expression) and in the biopharmaceutical industry (e.g. as immunogens, reagents for isolating B-cell specific activators or other transcriptional regulators, reagents for screening chemical libraries for lead pharmacological agents, etc.).

SEQ ID NO: LISTING

SEQ ID NO: 1: human EPAS1 cDNA.
SEQ ID NO: 2: murine EPAS1 cDNA.
SEQ ID NO: 3: HIF-1α binding site.
SEQ ID NO: 4: human EPAS1 protein.
SEQ ID NO: 5: murine EPAS1 protein.
SEQ ID NO: 6: human HIF-1α protein.
SEQ ID NO: 7: murine HIF-1α protein

DETAILED DESCRIPTION OF THE INVENTION

The nucleotide sequence of a natural cDNA encoding a human and murine EPAS1 proteins are shown as SEQ ID NOS: 1 and 2, respectively, and the full conceptual translates as SEQ ID NOS: 4 and 5, respectively. The EPAS1 proteins of the invention include incomplete translates of SEQ ID NOS: 1 and 2 and deletion mutants of SEQ ID NOS: 4 and 5, which translates and deletion mutants have EPAS1-specific amino acid sequence and binding specificity or function. Such active EPAS1 deletion mutants, EPAS1 peptides or protein domains comprise at least 14, preferably at least about 16, more preferably at least about 20 consecutive residues of SEQ ID NO: 4 or 5. For examples, EPAS1 protein domains identified below are shown to provide dimerization, protein-binding, and nucleic acid binding function. Additional such domains are identified in and find use, inter alia, in solid-phase binding assays as described below.

EPAS1-specific activity or function may be determined by convenient in vitro, cell-based, or in vivo assays: e.g. in vitro binding assays, cell culture assays, in animals (e.g. immune response, gene therapy, transgenics, etc.), etc. Binding assays encompass any assay where the molecular interaction of an EPAS1 protein with a binding target is evaluated. The binding target may be a natural intracellular binding target such as another bHLH/PAS protein, a heat shock protein, or a nucleic acid sequence/binding site or other regulator that directly modulates EPAS1 activity or its localization; or non-natural binding target such a specific immune protein such as an antibody, or an EPAS1 specific agent such as those identified in screening assays such as described below. EPAS1-binding specificity may assayed by binding equilibrium constants (usually at least about $10^7 M^{-1}$, preferably at least about $10^8 M^{-1}$, more preferably at least about $10^9 M^{-1}$), by the ability of the subject protein to function as negative mutants in EPAS1-expressing cells, to elicit EPAS1 specific antibody in a heterologous host (e.g a rodent or rabbit), etc. In any event, the EPAS1 binding specificity of the subject EPAS1 proteins necessarily distinguishes HIF-1α.

The claimed EPAS1 proteins are isolated or pure: an "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. The EPAS1 proteins and protein domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides natural and non-natural EPAS1-specific binding agents, methods of identifying and making such agents, and their use in diagnosis, therapy and pharmaceutical development. For example, EPAS1 -specific agents are useful in a variety of diagnostic and therapeutic applications. Novel EPAS1-specific binding agents include EPAS1-specific receptors, such as somatically recombined protein receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. For diagnostic uses, the binding agents are frequently labeled, such as with fluorescent, radioactive, chemiluminescent, or other easily detectable molecules, either conjugated directly to the binding agent or conjugated to a probe specific for the binding agent. Agents of particular interest modulate EPAS1 function, e.g. EPAS1-dependent transcriptional activation; for example, isolated cells, whole tissues, or individuals may be treated with an EPAS1 binding agent to activate, inhibit, or alter EPAS1-dependent transcriptional processes.

The amino acid sequences of the disclosed EPAS1 proteins are used to back-translate EPAS1 protein-encoding nucleic acids optimized for selected expression systems (Holier et al. (1993) Gene 136, 323–328; Martin et al. (1995) Gene 154, 150–166) or used to generate degenerate oligonucleotide primers and probes for use in the isolation of natural EPAS1-encoding nucleic acid sequences (GCG software, Genetics Computer Group, Inc, Madison Wis.). EPAS1-encoding nucleic acids used in EPAS1-expression vectors and incorporated into recombinant host cells, e.g. for expression and screening, transgenic animals, e.g. for functional studies such as the efficacy of candidate drugs for disease associated with EPAS1-modulated transcription, etc.

The invention also provides nucleic acid hybridization probes and replication/amplification primers having a EPAS1 cDNA specific sequence contained in SEQ ID NO: 1 and sufficient to effect specific hybridization thereto (i.e. specifically hybridize with SEQ ID NO: 1 in the presence of endothelial cell cDNA). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18M NaCl, 0.01M NaPO$_4$, pH 7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. EPAS1 cDNA homologs can also be distinguished from other protein using alignment algorithms, such as BLASTX (Altschul et al. (1990) Basic Local Alignment Search Tool, J Mol Biol 215, 403–410).

The subject nucleic acids are of synthetic/non-natural sequences an&or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO: 1 or 2 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of EPAS1 genes and gene transcripts and in detecting or amplifying nucleic acids encoding additional EPAS1 homologs and structural analogs. In diagnosis, EPAS1 hybridization probes find use in identifying wild-type and mutant EPAS1 alleles in clinical and laboratory samples. Mutant alleles are used to generate allele-specific oligonucleotide (ASO) probes for high-throughput clinical diagnoses. In therapy, therapeutic EPAS1 nucleic acids are used to modulate cellular expression or intracellular concentration or availability of active EPAS1.

The invention provides efficient methods of identifying agents, compounds or lead compounds for agents active at the level of a EPAS1 modulatable cellular function. Generally, these screening methods involve assaying for compounds which modulate EPAS1 interaction with a natural EPAS1 binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications include neoproliferative disease, inflammation, hypersensitivity, wound healing, immune deficiencies, infection etc.

In vitro binding assays employ a mixture of components including an EPAS1 proteins, which may be part of a fusion product with another peptide or polypeptide, e.g. a tag for detection or anchoring, etc. The assay mixtures comprise a natural intracellular EPAS1 binding target. While native binding targets may be used, it is frequently preferred to use portions (e.g. peptides) thereof so long as the portion provides binding affinity and avidity to the subject EPAS1 protein conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the EPAS1 protein specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the EPAS1 protein and one or more binding targets is detected by any convenient way. For cell-free binding type assays, a separation step is often used to separate bound from unbound components. Separation may be effected by precipitation (e.g. TCA precipitation, immunoprecipitation, etc.),immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). For EPAS1-dependent transcription assays, binding is detected by a change in the expression of an EPAS1-dependent reporter.

Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the EPAS1 protein to the target in the absence of the agent as compared with the binding affinity in the presence of the agent indicates that the agent modulates the binding of the EPAS1 protein to the EPAS1 binding target. Analogously, in the cell-based transcription assay also described below, a difference in the EPAS1 transcriptional induction in the presence and absence of an agent indicates the agent modulates EPAS1-induced transcription. A difference, as used herein, is statistically significant and preferably represents at least a 50%, more preferably at least a 90% difference.

The following experimental section and examples are offered by way of illustration and not by way of limitation.

EXPERIMENTAL cDNAs encompassing the coding region of the human EPAS1 were isolated by screening a HeLa cell cDNA library with a radiolabeled probe derived from an expressed sequence tag (#T70415) obtained from the Genbank data base (see Materials and Methods). Multiple cDNA clones were isolated and subjected to DNA sequence analysis to derive the conceptually translated protein sequence of human EPAS1 shown in Table 1. The predicted $M_r$ of the human EPAS1 was 96,528. A termination codon was located 24 nucleotides 5' of the designated initiator methionine in the human sequence. cDNAs encoding the murine homologue were isolated from an adult mouse brain cDNA library using a probe obtained by reverse transcriptase polymerase chain reactions with oligonucleotide primers derived from the human EPAS1 cDNA sequence (see Materials and Methods). The predicted protein sequence of murine EPAS1 is aligned and compared with the human sequence in Table 1. The two proteins share 88% sequence identity. Data base searches revealed that the human and murine EPAS1 proteins share extensive primary amino acid sequence identity with hypoxia inducible factor-1α (HIF-1α), a member of the bHLH/PAS domain family of transcription factors (Wang et al. 1995; Wenger et al. 1995). EPAS1 and HIF-1α share 48% primary amino acid sequence identity as revealed by the alignment shown in Table 1. Sequence conservation between the two proteins is highest in the basic-helix-loop-helix (85%), PAS A (68%) and PAS-B (73%) regions. A second region of sequence identity occurs at the extreme carboxy terminis of the EPAS1 and HIF-1α proteins. This conserved region in mHIF1α has been recently shown to contain a hypoxia response domain (Li et al., 1996). EPAS1 also shares sequence relatedness with other PAS domain proteins, however the degree of similarity between EPAS1 and other family members is less striking than that between HIF-1α and EPAS1.

Genomic clones encoding the human EPAS1 transcript were isolated by screening bacteriophage libraries of human DNA. The intron-exon structure of the gene was established by comparison of DNA sequences obtained from the genomic DNA to that of the cDNA. The coding region of EPAS1 is specified by 15 exons. The exonic sequences mapped to six non-overlapping bacteriophage lambda clones whose average insert size was 20 kb, indicating that the EPAS1 gene spans at least 120 kb of genomic DNA. A comparison of the EPAS1 gene structure with that of the aryl hydrocarbon receptor (Schmidt et al. 1993) reveals that the positions of introns within the regions encoding the amino-terminal halves of the two proteins are highly conserved. In contrast, the portion of the EPAS1 gene specifying the carboxy-terminal half of the protein is interrupted by seven introns, whereas the AHR gene contains only a single intron in this region. Thus the 5'-ends of the two genes may have arisen from an ancient gene duplication event, whereas the 3'-regions have a more recent evolutionary origin.

Two methods were used to determine the chromosomal location of the human EPAS1 gene. Fluorescent in situ hybridization (FISH) analysis was performed using a biotinylated probe containing exons 8–14 of the EPAS1 gene. This analysis revealed a single hybridization signal over chromosome 2, bands p16–p21. As a second assay for gene localization, an oligonucleotide primer pair derived from exon 8 was used to amplify a segment of the EPAS1 gene from the genomic DNAs of a radiation hybrid panel. Computer-assisted analysis of the results indicated linkage of the EPAS1 gene to the D2S288 marker on chromosome 2p with a LOD score of 8.7 and a cR8000 value of 12.96. Thus, the data obtained from two independent mapping methods consistently positioned the EPAS1 gene on the short arm of chromosome 2 and indicate that the EPAS1 gene is non-syntenic with the HIF-1α gene, which maps to chromosome 14q21–24 (Semenza et al. 1996).

The high degree of sequence similarity between the EPAS1 and HIF-1α proteins raises the possibility that they share a common physiological function. To test this hypothesis, RNA blotting experiments were used to compare and contrast the distributions of EPAS1 and HIF-1α mRNAs in a variety of human tissues. An EPAS1 mRNA of approximately 5.8 kb was detected in all tissues examined with the single exception of peripheral blood leukocytes. Among the positive tissues, highly vascularized organs such as the heart, placenta and lung showed the highest levels of EPAS1 mRNA. A HIF-1α mRNA of approximately 4.4 kb was detected in all human tissues. In contrast to EPAS1 mRNA, however, peripheral blood leukocytes contained very high levels of HIF-1α mRNA. Likewise, we observed no enrichment of HIF-1α mRNA in highly vascularized tissues.

These RNA blotting data indicate that, with few exceptions, most tissues express both EPAS1 and HIF-1α mRNAs. To determine if this overlap extended to the cellular level, in situ mRNA hybridization was used to determine the cell type specific expression patterns of the two gene products. Sections from day 11 and day 13 mouse embryos were examined first. In day 11 embryo sections, EPAS1 transcripts were observed almost exclusively in endothelial cells of the intersegmental blood vessels separating the somites, the atrial and ventricular chambers of the heart, and the dorsal aorta. Extra-embryonic membranes, such as the yolk sac, which are highly vascularized, also expressed abundant levels of EPAS1 mRNA. In the developing brain of a day 13 embryo, endothelial cells of the highly vascularized choroid plexus contained abundant EPAS1 transcripts. The brain section also revealed intense EPAS1 mRNA hybridization in the endothelial cells of a blood vessel lying along the edge of post-mitotic neurons emanating from the lateral ventricle region. When a nearby section was hybridized with an anti-sense probe that was specific for the HIF-1α mRNA, only a diffuse signal somewhat over background was detected, indicating a low level of HIF-1α expression in many cell types. In contrast to the results with the EPAS1 probe, no concentration of HIF-1α mRNA was detected in the endothelial cells of the adjacent blood vessel. A differential expression pattern between EPAS1 and HIF-1α was also apparent in the region of the embryo containing the umbilicus. EPAS1 transcripts were detected in the endothelium of blood vessels within this structure, whereas HIF-1α mRNA was concentrated in the mesenchyme surrounding the vascular endothelium.

In tissues of adult mice, EPAS1 mRNA was also detected at high levels in endothelial cells, yet was also present at lower levels in several additional cells types. For example, decidual cells of the placenta contained very high levels of EPAS1 mRNA as did parenchymal tissue in the lung. The distinction between EPAS1 expressing cell types and HIF-1α expressing cells was also apparent in adult tissues. A section through the cortex of the kidney showed EPAS1 expression in the mesangial cells. In contrast, HIF-1α expression was found in the cells of the collecting ducts. Taken together, these in situ mRNA hybridization results reveal very divergent patterns of EPAS1 and HIF-1α mRNA distribution.

The presence of basic helix-loop-helix and PAS domain motifs in EPAS1 raised the possibility that this protein might be capable of forming a complex with the aryl hydrocarbon receptor nuclear transport protein (ARNT) (Hoffman et al. 1991), and that the resulting heterodimer might exhibit sequence-specific DNA binding. To test these predictions, EPAS1 and ARNT expression vectors were used to program a reticulocyte lysate. The EPAS1 expression vector was modified at its carboxy-terminus with a c-Myc epitope tag to facilitate immunological detection of the EPAS1 translation product. Radiolabeled methionine was included in the translation mix containing the ARNT mRNA, whereas unlabeled methionine was used in the EPAS1 reaction. After translation, the two reactions were mixed and subsequently incubated with a monoclonal antibody that recognizes the c-Myc epitope present on the EPAS1 protein. Under these conditions the c-Myc antibody was capable of immunoprecipitating the radiolabeled ARNT protein only when EPAS1-Myc protein was present in the reaction.

The bHLH domains of HIF-1α and EPAS1 are nearly identical in primary amino acid sequence. Thus, to test for the ability of EPAS1 to form a functional heterodimer with ARNT, we used a HIF-1α response element derived from the 3'-flanking region of the erythropoietin gene (Semenza and Wang, 1992) in gel mobility shift assays with in vitro translated proteins. The data showed that a new complex was formed when both EPAS1 and ARNT were included in the DNA binding reaction, and that this complex was specifically recognized by an anti-peptide antibody directed against the EPAS1 protein. Competition experiments using a 100-fold excess of unlabeled competitor DNA containing the HIF-1α response element, or a response element with three point mutations in this sequence, indicated that EPAS1 exhibited sequence-specific binding properties. Taken together, the data indicate that EPAS1 is capable of binding the HIF-1α response element in the presence of the ARNT protein.

The ability of EPAS1 to trans-activate a reporter gene containing the HIF-1α response element was tested by transient transfection. Expression vectors in which either EPAS1, HIF-1α, or ARNT were placed under the control of a cytomegalovirus promoter were constructed. Two luciferase reporter constructs were prepared. One contained nucleotides −105 through +58 of the herpes simplex virus thymidine kinase promoter (McKnight et al. 1981) linked to three copies of the HIF-1α response element from the erythropoietin gene (pRE-tk-LUC). The other contained a TATA sequence from the adenovirus major late gene promoter (Lillie and Green, 1989) linked to the same three HIF-1α response elements (pE1B-LUC). Combinations of these plasmids were then transfected into cultured human embryonic kidney 293 cells and the expression of luciferase enzyme activity was monitored in cell lysates 16–20 hours post-transfection. The data showed that EPAS1 induced a 12-fold increase in luciferase enzyme activity when transfected in the absence of the ARNT vector. Cotransfection of the ARNT expression vector with low levels of EPAS1 expression vector did not increase the EPAS1-mediated induction of luciferase activity, suggesting that this cell line might contain adequate amounts of endogenous ARNT to support heterodimer formation with EPAS1. A seven-fold stimulation of luciferase activity was also obtained when larger amounts of the HIF-1α expression plasmid were introduced into 293 cells. The introduction of three point mutations into the core sequence of the hypoxia response element eliminated both EPAS1-dependent and HIF-1α-dependent activation of the reporter gene.

The potential of HIF-1α to induce expression of target genes is increased by both hypoxia and pharmacological compounds that mimic hypoxia in cells, such as desferrioxamine (DFX) and cobalt chloride ($CoCl_2$) (Wang et al. 1995). To determine if EPAS1 activity might also be stimulated by these agents, 293 cells were incubated under hypoxic conditions or treated with DFX or $CoCl_2$ prior to transfection with the plasmids. Pretreatment of cells under conditions that mimic hypoxia increased expression from the luciferase construct in the absence of exogenous EPAS1 or HIF-1α. This trans-activation presumably arises from endogenous HIF-1α or EPAS1 proteins whose mRNAs are present in 293 cells. As noted above, introduction of the EPAS1 expression vector led to 5- to 10 times higher levels of luciferase activity over those seen in mock-transfected cells. An extra 2 to 4-fold stimulation of luciferase expression was observed upon pretreatment with $CoCl_2$, DF, or hypoxia relative to that measured in EPAS1- transfected but untreated cells. Of the three conditions, pretreatment with $CoCl_2$ led to a slightly larger increase in EPAS1 activity, resulting in a four-fold higher level of luciferase activity over that detected in untreated cells. As has been observed in previous studies (Jiang et al. 1996; Forsythe et al. 1996), hypoxic conditions also stimulated the ability of HIF-1α to trans-activate the target gene containing the hypoxia response element.

The EPAS1 expression vector was also tested for its ability to activate a reporter gene (pRE-Elb-LUC) following transfection into murine hepatoma cells (Hepa1c1c7) that express ARNT, as well as in a mutant line derived from these parental cells that does not express ARNT (c4 variant, Legraverend et al. 1982). Expression of EPAS1 in the Hepa1c1c7 cells led to a nine-fold increase in luciferase activity. Transfection of EPAS1 alone into c4 cells increased luciferase enzyme activity only slightly (1.8-fold) whereas cotransfection of EPAS1 and ARNT led to a 12-fold stimulation of activity. These findings are consistent with the interpretation that EPAS1 forms an active heterodimeric transcription factor with ARNT, and they confirm the results showing heterodimerization of these two proteins obtained in coimmunoprecipitation and gel mobility shift assays.

The experiments demonstrating the functional activity of EPAS1 utilized a hypoxia response element derived from the erythropoietin gene, which is a known target gene for HIF-1α (Semenza and Wang, 1992). Despite the activity of EPAS1 in these assays, as well as the high degree of sequence similarity between HIF-1α and EPAS1, the in situ mRNA hybridization results indicate that the two proteins are expressed in different cell types and thus might activate different target genes. The high level of expression of EPAS1 in endothelial cells raises the possibility that the EPAS1 protein might activate genes whose expression is limited to endothelial cells. To test this hypothesis, we transfected 293 cells with a c-Myc-tagged EPAS1 expression vector and a marker gene composed of the 5'-flanking region of the Tie-2 gene linked to β-galactosidase. Tie-2 encodes a tyrosine kinase receptor that is specifically expressed in cells of endothelial lineage (Dumont et al. 1992; Maison-Pierre et al. 1993; Sato et al. 1993; Schnurch and Risau, 1993). The data showed that EPAS1 potently stimulated expression of the Tie-2-driven reporter gene, and that the degree of stimulation correlated with the level of immunodetectable EPAS1 in the transfected cells. Surprisingly, little or no transcriptional activation of the Tie-2 reporter gene by HIF-1α was detected, even though equivalent amounts of HIF-1α and EPAS1 proteins were expressed in the 293 cells.

These data reveal that EPAS1 proteins and nucleic acids provide reagents to modulate the formation of the endothelial tissues including vasculature, the blood brain barrier, etc. and to modulate cellular or tissue responsiveness to oxygenation, hypoxia and other hemodynamic stimuli.

cDNA and genomic cloning, chromosomal mapping

In the course of screening for genes that are differentially expressed in prostate adenocarcinoma versus normal tissue, a cDNA encoding a bHLH/PAS domain protein was isolated. Data base searches generated several expressed-sequence tags that showed sequence similarity to this family of transcription factors. EPAS1 cDNAs correspond to the human expressed sequence tag #T70415 in the Genbank collection and were isolated by a combination of reverse transcriptase polymerase chain reactions and screening of a HeLa cell cDNA library (Yokoyama et al. 1993) using standard methods. Similar approaches were used to isolate the murine homologue from a commercially available mouse adult brain cDNA library (#837314, Stratagene Corp., La Jolla, Calif.). A human HIF-1α cDNA was generated by ligation of an amplified cDNA fragment to expressed sequence tag hbc025 (Takeda et al. 1993). Bacteriophage clones harboring genomic DNA inserts corresponding to the human EPAS1 gene were isolated by screening a commercially available fibroblast genomic library (λFIXII vector, #946204, Stratagene Corp.)

Fluorescence in situ hybridization to identify the chromosomal localization of the human EPAS1 gene was carried out as previously described (Craig and Bickmore, 1994). This analysis indicated hybridization to the short arm of chromosome 2, bands p16–21. To confirm the assignment, a 269 bp segment of exon 8 from the EPAS1 gene was amplified from the 83 genomic DNAs of a radiation hybrid panel (Stanford G3 panel, Research Genetics, Huntsville, Ala.) using oligonucleotide primers and a thermocycler program consisting of 35 cycles of 94° C./1 min, 68° C./1 min. Analysis of the results via an e-mail server at Stanford University indicated linkage to the D2S288 marker (logarithm of the odds score of 8.7, cR_8000 value of 12.96), which is located approximately 82 centimorgans from the telomere of the short arm of chromosome 2 (MIT Center for Genome Research).

RNA blotting and in situ hybridization

Human multiple tissue RNA blots (Clontech Laboratories, Palo Alto, Calif.) were probed with EPAS1 and HIF-1α cDNA probes using Rapid-Hyb from Amersham Corp. (Arlington Heights, Ill.). For in situ mRNA hybridization, mouse tissues were fixed in 4% paraformaldehyde, sectioned at 5 μm thickness, and subjected to in situ mRNA hybridization as described (Berman et al. 1995). A [$^{33}$P]-labeled antisense RNA probe recognizing the EPAS1 mRNA was derived by in vitro transcription of an ~300. bp DNA fragment encoding amino acids 225–327 of the sequence shown in Table 1. A segment of the murine HIF-1α cDNA encoding amino acids 41–125 was isolated by reverse transcriptase-polymerase chain reactions using mRNA template isolated from embryonic day 10 mouse embryo.

Co-immunoprecipitation experiments

Human EPAS1 and mouse ARNT proteins were generated in vitro using a transcription-translation kit (TNT System, Promega Corp., Madison, Wis.). cDNAs encoding full-length proteins were subcloned into the pcDNA3 vector (Invitrogen Corp., San Diego, Calif.) prior to coupled transcription/translation. For immunoprecipitation, approximately 5 μl of each reaction were transferred to a separate tube, mixed well and subsequently diluted by the addition of 500 μl of ice-cold buffer (20 mM Hepes-KOH, pH 7.4/100 mM KCl/10% (v/v) glycerol/0.4% (v/v) Nonidet P-40/5 mM EGTA/5 mM EDTA/100 µg/ml bovine serum albumin/1 mM dithiothreitol) (Huang et al. 1993). The diluted mixture was incubated with 1 µl (0.1 µg) of anti-Myc monoclonal antibody 9E10 (Santa Cruz Biotechnology, Santa Cruz, Calif.) for 2 hours at 4° C. A 10 µl aliquot of beads (~4×10$^6$ in number, Dynal Corp., Lake Success, N.Y.) coated with rat anti-mouse IgG1 antibody were then added followed by a further incubation for 1 hour at 4° C. Beads were washed three times with 1.5 ml of the above buffer and bound proteins were subsequently analyzed by electrophoresis through 8% polyacrylamide gels containing SDS.

Gel retention assays

EPAS1 and ARNT cDNAs were translated in vitro as described above. Gel retention assays were performed as described previously (Semenza and Wang, 1992) using a double-stranded oligonucleotide probe radiolabeled with the Klenow fragment of *E. coli* DNA polymerase I and containing an HIF-1α binding site (5'-GCCCTACGTGCTGTCTCA-3', SEQ ID NO: 3) from the erythropoietin gene (Semenza and Wang, 1992). For supershift assays, a polyclonal antibody was raised against residues 1 to 10 of the human EPAS1 protein by standard methods and 1 µl of serum was added to the gel retention reaction mixture prior to the 30 minute incubation at 4° C. A preimmune serum served as a negative antibody control.

Transient transfection assays

The pTK-RE3-luc reporter plasmid was constructed by inserting three copies of a 50-nucleotide hypoxia-inducible enhancer from the erythropoietin gene (Semenza and Wang, 1992) into pGL3-TK. The Tie-2-β-galactosidase reporter gene pT2HLacZpA1L7, containing 10.3 kb of 5'-flanking DNA from the murine Tie-2 gene was obtained from the Cardiovascular Division, Beth Israel Hospital, Boston, Mass. Human embryonic kidney 293 cells (ATCC CRL#1573) were cultured in Dulbecco's modified Eagle's medium (DMEM, low glucose; Gibco-BRL) supplemented with 10% fetal calf serum. The murine hepatoma cell line Hepa1c1c7 and the c4 ARNT deficient mutant derived from this line were maintained as described previously (Legraverend et al. 1982). Approximately 24 hours before transfection, cells were inoculated in 12-well plates at a density of 120,000 cells per well. Plasmid DNA (1–10 µg) was transfected into cells using a kit (MBS, Stratagene Corp., La Jolla, Calif.). Cells were allowed to recover for 3 hours at 35° C. in a 3% $CO_2$ atmosphere. Where indicated, 125 µM $CoCl_2$ (#C3169, Sigma Chem. Corp., St. Louis, Mo.) or 130 µM desferrioxamine (#D9533, Sigma) were added to cells at this time and the incubation continued for an additional 16 hours in atmospheres containing 20% or 1% $O_2$. Luciferase and β-galactosidase enzyme activities were determined according to the manufacturer's instructions (Tropix, Bedford, Mass.). Reporter gene expression was normalized by cotransfection of a β-galactosidase expression vector (pCMV-β-gal) and/or to expression obtained from the pGL3-Control plasmid (Promega Corp., Madison, Wis.). Levels of expressed c-Myc epitope-tagged EPAS1 or HIF-1α were assessed by immunoblotting with the anti-Myc monoclonal antibody 9E10 (Santa Cruz Biotechnology, Santa Cruz, Calif.) using a protocol supplied by the manufacturer.

References

Antonsson, C., V. et al. 1995. *J. Biol. Chem.* 270:13968–13972.
Berman, D. M., H. Tian, and D. W. Russell 1995. *Mol. Endocrinol.* 9:1561–1570.
Brogi, E., G. et al. 1996. *J. Clin. Invest.* 97:469–476.
Burbach, K. M., A. Poland, and C. A. Bradfield 1992. *Proc. Natl. Acad. Sc. U.S.A.* 89:8185–8189.
Chen, H. S., and G. H. Perdew 1994.*J. Biol. Chem.* 269:27554–27558.
Citri, Y., et al. 1987. *Nature* 326:42–47.
Craig, C. M., and W. A. Bickmore 1994. *Nature Genetics* 7:376–382.
Dumont, D. J., et al. *Genes & Dev.* 8:1897–1909.
Dumont, D. J., et al. 1995. *Developmental Dynamics* 203:80–92.
Dumont, D. J., et al. 1992. *Oncogene* 7:1471–1480.
Fong, G-H., J. Reascend, M. Gertsenstein, and M. L. Breitman 1995. *Nature* 376:66–70.
Forsythe, J. A., et al. 1996. *Molec. Cell Biol.* 16:4604–4613.
Fukunaga, B. N., et al. 1995. *J. Biol. Chem.* 270:29270–29278.
Gekakis, N., et al. 1995. *Science* 270:811–815.
Hankinson, O. 1995. *Ann. Rev. Pharmacol. Toxicol.* 35:307–340.
Henry, E. G., and T. A. Gasiewicz 1993. *Biochem. J.* 294: (Pt 1) 95–101.
Hirose, K., et al. 1996. *Cell Biol.* 16:1706–1713.
Hoffman, E. C., et al. 1991. *Science* 252:954–958.
Huang, Z. J., I. Edery, and M. Rosbash 1993. *Nature* 364:259–262.
Hunter-Ensor, M., A. Ousley, and A. Sehgal 1996. *Cell* 84:677–685.
Isaac, D. D., and D. J. Andrew 1996. *Genes & Dev.* 10:103–117.
Jackson, F. R., T. A. Bargiello, S. H. Yun, and M. W. Young 1986. *Nature* 320:185–188.
Jiang, B-H., E. Rue, G. L. Wang, R. Roe, and G. L. Semenza 1996. *J. Biol. Chem.* 271:17771–1778.
Konopka, R. J., and S. Benzer 1971. *Proc. Natl. Acad. Sci. U.S.A.* 68:2112–2116.
Lee, C., V. Parikh, T. Itsukaichi, K. Bae, and I. Edery 1996. *Science* 271:1740–1744
Legraverend, C., et al. 1982. *J. Biol. Chem.* 257:6402–6407.
Lillie, J. W., and M. R. Green 1989. *Nature* 338:39–44.
Lindebro, M. C., L. Poellinger, and M. L. Whitelaw 1995.*EMBO J.* 14:3528–3539.
Maison-Pierre, P. C., M. Goldfarb, G. D. Yancopoulos, and G. Gao 1993. *Oncogene* 8:1631–1637.
McGuire, J., et al. 1995. *J. Biol. Chem.* 270:31353–31357.
McKnight. S. L., E. R. Gavis, R. Kingsbury, and R. Axel 1981. *Cell* 25:385–398.
Myers, M. P., et al. 1995. *Science* 270:805–808.
Myers, M. P., et al. 1996. *Science* 271:1736–1740.
Nambu, J. R., J. O. Lewis, K. A. Wharton, and S. T. Crews 1991. *Cell* 67:1157–1167.
Namiki, A., et al. 1995. *J. Biol. Chem.* 270:31189–31195.
Perdew, G. H. 1988. *J. Biol. Chem.* 263:13802–13805.
Reisz-Porszasz, S., et al. 1994. *Mol. Cell Biol.* 14:6075–6086.
Sato, T. N., et al. 1995. *Nature* 376:70–74.
Sato, T. N., et al. 1993. *Proc. Natl. Acad. Sci. U.S.A.* 90:9355–9358.
Schmidt, J. V., and C. A. Bradfield 1996. Ah. *Annu. Rev. Cell Dev. Biol.* 12: in press.
Schmidt, J. V., L. A. Carver, and C. A. Bradfield 1993. *J. Biol. Chem.* 268:22203–22209.
Schnurch, H., and W. Risau 1993. *Development* 119:957–968.
Semenza, G. L., E. A. Rue, N. V. Iyer, M. G. Pang, and W. G. Kearns 1996. *Genomics* 34:437–439.
Semenza, G. L. 1994. *Hematology-Oncology Clinics of North America* 8:863–884.

Semenza, G. L., and G. L. Wang 1992. *Mol. Cell. Biol.* 12:5447–5454.

Shalaby, F., et al. 1995. *Nature* 376:62–66.

Sogawa, K., et al. 1995. *Proc. Natl. Acad. Sci. U.S.A.* 92:1936–1940.

Takeda, J., H. Yano, S. Eng, Y. Zeng, and G. I. Bell 1993. *Hum Mol. Genet.* 2: 1793–1798/

Wang, G. L., and G. L. Semenza 1995. *J. Biol. Chem.* 270:1230–1237.

Wang, G. L., et al. 1995. *Proc. Natl. Acad. Sci. U.S.A.* 92:5510–5514.

Wenger, R. H., et al. 1996. *Biochem. Biophys. Res. Commun.* 223:54–59.

Wilk, R., I. Weizman, and B-Z. Shilo 1996. *Genes & Dev.* 10:93–102.

Wood, S. M., et al. 1996. *J. Biol. Chem.* 271:15117–15123.

Yokoyama, C., et al. 1993. *Cell* 75:187–197.

Zeng, H., Z. Qian, M. P. Myers, and M. Rosbash 1996. *Nature* 380:129–135.

EXAMPLES

1. Protocol for high throughput EPAS1-ARNT complex formation assay.

A. Reagents:

Neutralite Avidin: 20 µg/m in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P EPAS1 protein 10×stock: $10^{-8}$–$10^{-6}$M "cold" EPAS1 supplemented with 200,000–250,000 cpm of labeled EPAS1 (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

ARNT: $10^{-7}$–$10^{-5}$M biotinylated ARNT in PBS.

B. Preparation of assay plates:

Coat with 120 µl of stock N-Avidin per well overnight at 4° C.

Wash 2 times with 200 µl PBS.

Block with 150 µl of blocking buffer.

Wash 2 times with 200 µl PBS.

C. Assay:

Add 40 µl assay buffer/well.

Add 10 µl compound or extract.

Add 10 µl $^{33}$P-EPAS1 protein (20–25,000 cpm/0.1–10 pmoles/well=$10^{-9}$–$10^{-7}$M final conc).

Shake at 25° C. for 15 minutes.

Incubate additional 45 minutes at 25° C.

Add 40 µl biotinylated hTFII subunit (0.1–10 pmoles/40 µl in assay buffer)

Incubate 1 hour at room temperature.

Stop the reaction by washing 4 times with 200 µl PBS.

Add 150 µl scintillation cocktail.

Count in Topcount.

D. Controls for all assays (located on each plate):

a. Non-specific binding b. Soluble (non-biotinylated EPAS1) at 80% inhibition.

2. Protocol for high throughput human EPAS1/ARNT-DNA complex formation assay.

A. Reagents:

Neutralite Avidin: 20 µg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P human EPAS1 protein 10×stock: $10^{-8}$–$10^{-6}$M "cold" human EPAS1 subunit (p105) supplemented with 200,000–250,000 cpm of labeled human EPAS1 (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

DNA: $10^{-7}$–$10^{-4}$M biotinylated DNA (SEQ ID NO: 3) in PBS.

ARNT protein: $10^{-7}$–$10^{-5}$M ARNT in PBS.

B. Preparation of assay plates:

Coat with 120 µl of stock N-Avidin per well overnight at 4° C.

Wash 2 times with 200 µl PBS.

Block with 150 µl of blocking buffer.

Wash 2 times with 200 µl PBS.

C. Assay:

Add 40 µl assay buffer/well.

Add 10 µl compound or extract.

Add 10 µl $^{33}$P-h EPAS1 protein (20–25,000 cpm/0.1–10 pmoles/well=$10^{-9}$–$10^{-7}$M final).

Add 10 µl ARNT protein.

Shake at 25° C. for 15 minutes.

Incubate additional 45 minutes at 25° C.

Add 40 µl biotinylated DNA (0.1–10 pmoles/40 µl in assay buffer)

Incubate 1 hour at room temperature.

Stop the reaction by washing 4 times with 200 µl PBS.

Add 150 µl scintillation cocktail.

Count in Topcount.

D. Controls for all assays (located on each plate):

a. Non-specific binding b. Soluble (non-biotinylated EPAS1/ARNT combination) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

```
  1  MTAD---KEKKRSSSERRKEKSRDAARCRRSKETEVFYELAHELPLPHSVSSHLDKASIMRLEISFLRTHKLLSSVCSENESEAEADQQM       hEP-1 SEQ ID NO:4
  1  MTAD---KEKKRSSELRKEKSRDAARCRRSKETEVFYELAHELPLPHSVSSHLDKASIMRLAISFLRTHKLLSSVCSENESEAEADQQM       mEP-1SEQ ID NO:5
  1  MEGAGANDKKKISSERRKEKSRDAARSRRSKESEVFYELAHQLPLPHNVSSHLDKASVMRITISYLRVRKLLDA--GDLDIEDDMKAQM       hHIF SEQ ID NO:6
  1  M------SSERRKEKSRDAARSRRTKESEVFYELAHQLPLPHNVSSHLDKASVMRLTISYLRVRKLLDA--GGLDSEDEMKAQM           mHIF SEQ ID NO:7

88  DNLYLKALEGFIAVVTQDGDMIFLSENISKFMGLTQVELTGHSIFDFTHPCDHEEIRENLSLKNGSGFGKKSKDMSTERDFFMRMKCTVT    hEP-1
 88  DNLYLKALEGFIAVVTQDGDMIFLSENISKFMGLTQVELTGHSIFDFTHPCDHEEIRENLTLKNGSGFGKKSKDVSTERDFFMRMKCTVI    mEP-1
 89  NCFYLKALDGFVMVLTDDGDMIYISDNVNKYMGLTQFELTGHSVFDFTHPCDHEEMREMLTHRNGLV--KKGKEQNTQRSFFLRMKCTLI    hHIF
 77  DCFYLKALDGFVMVLTDDGDMVYISDNVNKYMGLTQFELAGHSVFDFTHPCDHEEMREMLTHRNGPV--RKGKELNTQRSFFLRMKCTLT    mHIF

178  NRGRTYVNLKSATWK-VLHCTGQVKVYNNCPPHNSLCGYKEPLLSCLIIMCEPIQHPSHMDIPLDSKTFLSRHSMDMKFTYCDDRITELIG   hEP-1
178  NPGRTYVNLKSATWKSVLHCTGQVRVYNNCPPHSSLCGSKEPLLSCLIIMCEPIQHPSHMDIPLDSKTFLSRHSMDMKFTYCDDRILELIG   mEP-1
177  SRGRTMNIKSATWK-VLHCTGHIHVYDT-NSNQPQCGYKKKPPMTCLVLICEPIPHPSNIEIPLDSKTFLSRHSLDMKFSYCDERITELMG   hHIF
165  SRGRTMNIKSATWK-VLHCTGHIHVYDT-NSNQPQCGYKKPPMTCLVLICEPIPHPSNIEIPLDSKTFLSRHSLDMKFSYCDERITELMG    mHIF

267  YHPEELLGRSAYEFYHALDSENMTKSHQNLCTKGQVVSGQYRMLAKHGGYVWLETQGTVIYNPRNLQPQCIMCVNYVLSEIEKNDVVFSM    hEP-1
268  YHPEELLGRSAYEFYHALDSENMTKSHQNLCTKGQVVSGQYRMLAKHGGYVWLETQGTVIYNPRNLQPQCIMCVNYVLSEIEKNDVVFSM    mEP-1
265  YEPEELLGRSIYEYYHALDSDHLTKTHHDMFTKGQVTTGQYRMIAKRGGYVWETQATVIYNTKNSQPQCIVCVNYVVSGIIQHDLIFSL     hHIF
253  YEPEELLGRSIYEYYHALDSDHLTKTHHDMFTKGQVTTGQYRMLAKRGGYVWETQATVIYNTKNSQPQCIVCVNYVVSGIIQHDLIFSL     mHIF

357  DQTESLFKP---HLMAMNSIFDSSGKGAVSEKSNFLFTKLKWPEELAQLAPTGDAIISLDFGN------QNFEESAYGKAILPPSQ        hEP-1
358  DQIELSFKP---HLMAMNSIFDSSDDVAVTEKSNYLFTKLFEEPEELAQLAPTPGDAIISLDFGS------QNFDEPSAYGKALLPPGQ      mEP-1
355  QQTECVLKPVESSDMKMTQLFTKVE---SEDTSSLFDKLFKEPDALTLLAPAAGDTIISLDFGSNDTETDDQQLEEVPLYNDVMLPSPN     hHIF
343  QQTESVLKPVESSDMKMTQLFTKVE---SEDTSCLFDKLKKEPDALTLLAPAAGDTIISLDFGSDDTETEDQQLEDVPLYNDVMFPSSN     mHIF

437  --------PWATE----LRSHST-----------QSEAGSLP-AFTVPQAAAPGSTTPSATSSSSCSTPNSPEDYYTSIDNDL--         hEP-1
438  --------PWVSG---LRSHSA-----------QSESGSLP-AFTVPQADTPGNTTPSA-SSSSSCSTPSSPEDYYSSLENPL--         mEP-1
441  EKLQNINLAMSPLPTAETPKPLRSSADPALNQEVALKLEPNPESELSFTMPQIQDDQTPSPSDG-STRQSSPEPNSPSEYCFYVDSDMVN    hHIF
429  EKL-NINLAMSPLPSSETPKPLRSSADPALNQEVALKLESSPEBSLGLSFTMPQIQDQPASPSDG-STRQSSPEPNSPSEYCFDVDSDMVN   mHIF
```

TABLE 1-continued

```
497 --KIEVIEKLFAMDTEAKDQCSTQTDFNELDLETLAPYIPMDGEDFQLSPICPEERLLAENPQS---TPQHCFSA--MINIFQPL-APVA      hEP-1
497 --KIEVIEKLFAMDTEAKDQCSTQTDFSELDLETLAPYIPMDGEDFQLSPICPEEPLMPESPQP---TPQHCFST--MISIFQPL-TPGA      mEP-1
530 EFKLELVEKLFAEDTEAKNPFSTQD---TDLDLEMLAPYIPMD-DDGQLRSFDQLSPLESSASPESASPQSTVTVFQQTQIQEPT-ANAT      hHIF
517 VFKLELVEKLFAEDIEAKNPFSTQD---TDLDLEMLAPYIPMD-DDFQERSFDQLSPLESNSPSP----PSMSTVTGFQQTIQLQKPTITATA   mHIH

579 PHSPFLLDKFQQQLESKKTEPEHRPMSSIFFDAGSKASLPPCCGQASTPLSSMGGRSNTQWPDPPLHFGPTKWAVGDQRTEFLGAAPLG       hEP-1
579 THGPFFLDKYPQQLESRKTESEHWPMSSIFFDAGSKGSLSPCCGQASTPLSSMGGRSNTQWPDPPLHFGPTKWPVGDDQSAESIGALPVG      mEP-1
616 TTTA------TTDELKTVTKDRMEDIKILIASPSTHIH----KETTSATSSPYRDTQSRTASP------NRAGKGVIEQTEKS             hHIF
601 TTTA------TTDESKTETKDNKEDIKILIASPSTQVP----QETTTAKASAYSGTHSRTASP------DRAGKRVIEQTDKA             mHIH

669 P----PVSPP-HVSTFKTRSAKGFGARGPDVLSPAMVALSNKLKLKRQLEYEEQAFQDLSGG----DPPG--GSTSHLMWKRMKNLRGGS      hEP-1
669 SWQLELPSAPL-HYSMFKMRSAKDFGARGPYMMSPAMIALSNKLKLKRQLEYEBQAFQDTSGG---DPPG--TSSSHLMWKRMKSLMGGT      mEP-1
684 H------PRSPNVLSVALSQRTIVP----EEEINPKILALQNAQR-KRKMEHDGSLFQAVGIGTLLQQPDDHAAITSLSWKRVKGCKS--      hHIF
669 H------PRSLN-LSATLNQRNTVP----EEEINPKTIASQNAQR-KRKMEHDGSLFQAAGIGTLLQQPGDCAPITMSLSWKRVKGFIS--    mHIH

748 CPLMPDKPLSANVPNDKFTQNPMRGLGHPLRHIPLPQPPSAISPGENSKSRFPPQCYATQYQDYSLSSAHKVSGMASRLLGPSFESYLLP      hEP-1
753 CPLMPDKTISANMAPDEFTQKSMRGLGQPLRHLPPQPPSTRSSGENAKTGFPPQCYASQFPQDYGPPGAQKVSGVASRLLGPSFEPYLLP      mEP-1
761 ----------------------------------SEQNGMEQKTIIILIP--------SDLACRLLGQSMDESGLP                   hHIF
745 ----------------------------------SEQNGTEQKTIIILIP--------SDLACRLLGQSMDVSGLP                   mHIF

838 ELTRYDCEVNVPVLGSSTLLQCGDLLRALDQAT   hEP-1
843 ELTRYDCEVNVPVPGSSTLLQCRDLLRALDQAT   mEP-1
794 QLTSYDCEVNAPIQGSRNLLQCEELLRALDQVN   hHIF
778 QLTSYDCEVNAPIQGSRNLLQCEELLRALDQVN   mHIF
```

What is claimed is:

1. An isolated protein comprising a endothelial PAS domain protein 1 (EPAS1) protein (SEQ ID NO: 4 or 5), or an EPAS1 protein domain thereof having at least 14 consecutive amino acids of SEQ ID NO: 4 or 5 and an EPAS1-specific activity.

2. The isolated protein according to claim 1, wherein said protein specifically binds at least one of a bHLH/PAS protein, a heat shock protein, or a nucleic acid consisting of SEQ ID NO: 3.

3. A recombinant nucleic acid encoding a protein according to claim 1.

4. A method of screening for an agent which modulates the binding of a EPAS1 protein to a binding target, said method comprising the steps of:

incubating a mixture comprising:
the isolated protein according to claim 1,
a binding target of said protein, and
a candidate agent;
under conditions whereby, but for the presence of said agent, said protein specifically binds said binding target at a reference affinity;
detecting the binding affinity of said protein to said binding target to determine an agent-biased affinity,
wherein a difference between the agent-biased affinity and the reference affinity indicates that said agent modulates the binding of said protein to said binding target.

5. A cell comprising a nucleic acid according to claim 3.

6. The method according to claim 4, wherein said binding target is a one of a bHLH/PAS protein, a heat shock protein, or a nucleic acid consisting of SEQ ID NO: 3.

7. A method of making an isolated EPAS1 protein, comprising steps: introducing a nucleic acid according to claim 3 into a host cell or cellular extract, incubating said host cell or extract under conditions whereby said nucleic acid is expressed as a transcript and said transcript is expressed as a translation product comprising said protein, and isolating said translation product.

8. An isolated EPAS1 protein made by the method of claim 7.

9. An isolated EPAS1 nucleic acid comprising SEQ ID NO: 1 or 2, or a fragment thereof having at least 24 consecutive bases of SEQ ID NO: 1 or 2 and sufficient to specifically hybridize with a nucleic acid having the sequence defined by the corresponding SEQ ID NO: 1 or 2 in the presence of human or murine genomic DNA, respectively.

10. The isolated EPAS1 nucleic acid according to claim 9, said nucleic acid comprising SEQ ID NO: 1, or a fragment thereof having at least 24 consecutive bases of SEQ ID NO: 1 and sufficient to specifically hybridize with a nucleic acid having the sequence defined by SEQ ID NO: 1 in the presence of human genomic DNA.

11. The isolated EPAS1 nucleic acid according to claim 9, said nucleic acid comprising SEQ ID NO: 2, or a fragment thereof having at least 24 consecutive bases of SEQ ID NO: 2 and sufficient to specifically hybridize with a nucleic acid having the sequence defined by SEQ ID NO: 2 in the presence of murine genomic DNA.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 2816 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| CCTGACTGCG | CGGGGCGCTC | GGGACCTGCG | CGCACCTCGG | ACCTTCACCA | CCCGCCCGGG | 60 |
| CCGCGGGGAG | CGGACGAGGG | CCACAGCCCC | CCACCCGCCA | GGGAGCCCAG | GTGCTCGGCG | 120 |
| TCTGAACGTC | TCAAAGGGCC | ACAGCGACAA | TGACAGCTGA | CAAGGAGAAG | AAAAGGAGTA | 180 |
| GCTCGGAGAG | GAGGAAGGAG | AAGTCCCGGG | ATGCTGCGCG | GTGCCGGCGG | AGCAAGGAGA | 240 |
| CGGAGGTGTT | CTATGAGCTG | GCCCATGAGC | TGCCTCTGCC | CCACAGTGTG | AGCTCCCATC | 300 |
| TGGACAAGGC | CTCCATCATG | CGACTGGAAA | TCAGCTTCCT | GCGAACACAC | AAGCTCCTCT | 360 |
| CCTCAGTTTG | CTCTGAAAAC | GAGTCCGAAG | CCGAAGCTGA | CCAGCAGATG | GACAACTTGT | 420 |
| ACCTGAAAGC | CTTGGAGGGT | TTCATTGCCG | TGGTGACCCA | AGATGGCGAC | ATGATCTTTC | 480 |
| TGTCAGAAAA | CATCAGCAAG | TTCATGGGAC | TTACACAGGT | GGAGCTAACA | GGACATAGTA | 540 |
| TCTTTGACTT | CACTCATCCC | TGCGACCATG | AGGAGATTCG | TGAGAACCTG | AGTCTCAAAA | 600 |
| ATGGCTCTGG | TTTTGGGAAA | AAAAGCAAAG | ACATGTCCAC | AGAGCGGGAC | TTCTTCATGA | 660 |
| GGATGAAGTG | CACGGTCACC | AACAGAGGCC | GTACTGTCAA | CCTCAAGTCA | GCCACCTGGA | 720 |
| AGGTCTTGCA | CTGCACGGGC | CAGGTGAAAG | TCTACAACAA | CTGCCCTCCT | CACAATAGTC | 780 |
| TGTGTGGCTA | CAAGGAGCCC | CTGCTGTCCT | GCCTCATCAT | CATGTGTGAA | CCAATCCAGC | 840 |
| ACCCATCCCA | CATGGACATC | CCCCTGGATA | GCAAGACCTT | CCTGAGCCGC | CACAGCATGG | 900 |
| ACATGAAGTT | CACCTACTGT | GATGACAGAA | TCACAGAACT | GATTGGTTAC | CACCCTGAGG | 960 |
| AGCTGCTTGG | CCGCTCAGCC | TATGAATTCT | ACCATGCGCT | AGACTCCGAG | AACATGACCA | 1020 |
| AGAGTCACCA | GAACTTGTGC | ACCAAGGGTC | AGGTAGTAAG | TGGCCAGTAC | CGGATGCTCG | 1080 |
| CAAAGCATGG | GGGCTACGTG | TGGCTGGAGA | CCCAGGGGAC | GGTCATCTAC | AACCCTCGCA | 1140 |
| ACCTGCAGCC | CCAGTGCATC | ATGTGTGTCA | ACTACGTCCT | GAGTGAGATT | GAGAAGAATG | 1200 |
| ACGTGGTGTT | CTCCATGGAC | CAGACTGAAT | CCCTGTTCAA | GCCCCACCTG | ATGGCCATGA | 1260 |
| ACAGCATCTT | TGATAGCAGT | GGCAAGGGGG | CTGTGTCTGA | GAAGAGTAAC | TTCCTATTCA | 1320 |
| CCAAGCTAAA | GGAGGAGCCC | GAGGAGCTGG | CCCAGCTGGC | TCCCACCCCA | GGAGACGCCA | 1380 |
| TCATCTCTCT | GGATTTCGGG | AATCAGAACT | TCGAGGAGTC | CTCAGCCTAT | GGCAAGGCCA | 1440 |
| TCCTGCCCCC | GAGCCAGCCA | TGGGCCACGG | AGTTGAGGAG | CCACAGCACC | CAGAGCGAGG | 1500 |
| CTGGGAGCCT | GCCTGCCTTC | ACCGTGCCCC | AGGCAGCTGC | CCCGGGCAGC | ACCACCCCA | 1560 |
| GTGCCACCAG | CAGCAGCAGC | AGCTGCTCCA | CGCCCAATAG | CCCTGAAGAC | TATTACACAT | 1620 |
| CTTTGGATAA | CGACCTGAAG | ATTGAAGTGA | TTGAGAAGCT | CTTCGCCATG | GACACAGAGG | 1680 |
| CCAAGGACCA | ATGCAGTACC | CAGACGGATT | TCAATGAGCT | GGACTTGGAG | ACACTGGCAC | 1740 |
| CCTATATCCC | CATGGACGGG | GAAGACTTCC | AGCTAAGCCC | CATCTGCCCC | GAGGAGCGGC | 1800 |

| | | | | | | |
|---|---|---|---|---|---|---|
| TCTTGGCGGA | GAACCCACAG | TCCACCCCCC | AGCACTGCTT | CAGTGCCATG | ACAAACATCT | 1860 |
| TCCAGCCACT | GGCCCCTGTA | GCCCCGCACA | GTCCCTTCCT | CCTGGACAAG | TTTCAGCAGC | 1920 |
| AGCTGGAGAG | CAAGAAGACA | GAGCCCGAGC | ACCGGCCCAT | GTCCTCCATC | TTCTTTGATG | 1980 |
| CCGGAAGCAA | AGCATCCCTG | CCACCGTGCT | GTGGCCAGGC | CAGCACCCCT | CTCTCTTCCA | 2040 |
| TGGGGGGCAG | ATCCAATACC | CAGTGGCCCC | CAGATCCACC | ATTACATTTT | GGGCCCACAA | 2100 |
| AGTGGGCCGT | CGGGGATCAG | CGCACAGAGT | TCTTGGGAGC | AGCGCCGTTG | GGGCCCCCTG | 2160 |
| TCTCTCCACC | CCATGTCTCC | ACCTTCAAGA | CAAGGTCTGC | AAAGGGTTTT | GGGGCTCGAG | 2220 |
| GCCCAGACGT | GCTGAGTCCG | GCCATGGTAG | CCCTCTCCAA | CAAGCTGAAG | CTGAAGCGAC | 2280 |
| AGCTGGAGTA | TGAAGAGCAA | GCCTTCCAGG | ACCTGAGCGG | GGGGACCCA | CCTGGTGGCA | 2340 |
| GCACCTCACA | TTTGATGTGG | AAACGGATGA | AGAACCTCAG | GGGTGGGAGC | TGCCCTTTGA | 2400 |
| TGCCGGACAA | GCCACTGAGC | GCAAATGTAC | CCAATGATAA | GTTCACCCAA | ACCCCATGA | 2460 |
| GGGGCCTGGG | CCATCCCCTG | AGACATCTGC | CGCTGCCACA | GCCTCCATCT | GCCATCAGTC | 2520 |
| CCGGGGAGAA | CAGCAAGAGC | AGGTTCCCCC | CACAGTGCTA | CGCCACCCAG | TACCAGGACT | 2580 |
| ACAGCCTGTC | GTCAGCCAC | AAGGTGTCAG | GCATGGCAAG | CCGGCTGCTC | GGGCCCTCAT | 2640 |
| TTGAGTCCTA | CCTGCTGCCC | GAACTGACCA | GATATGACTG | TGAGGTGAAC | GTGCCCGTGC | 2700 |
| TGGGAAGCTC | CACGCTCCTG | CAAGGAGGGG | ACCTCCTCAG | AGCCCTGGAC | CAGGCCACCT | 2760 |
| GAGCCAGGCC | TTCTACCTGG | GCAGCACCTC | TGCCGACGCC | GTCCCACCAG | CTTCAC | 2816 |

( 2 ) INFORMATION FOR SEQ ID NO:2:

( i ) SEQUENCE CHARACTERISTICS:
        ( A ) LENGTH: 3031 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| CGACAGAGAG | CTGCGGAGGG | CCACAGCAAA | GAGAGCGGCT | GCAGCCCCTA | CGGGGTTAAG | 60 |
| GAACCCAGGT | GCTCCGGGTC | TCGGAGGGCC | ACGGCGACAA | TGACAGCTGA | CAAGGAGAAA | 120 |
| AAAAGGAGCA | GCTCAGAGCT | GAGGAAGGAG | AAATCCCGTG | ATGCCGCGAG | GTGCCGGCGC | 180 |
| AGCAAGGAGA | CGGAGGTCTT | CTATGAGTTG | GCTCATGAGT | TGCCCCTGCC | TCACAGTGTG | 240 |
| AGCTCCCACC | TGGACAAAGC | CTCCATCATG | CGCCTGGCCA | TCAGCTTCCT | TCGGACACAT | 300 |
| AAGCTCCTGT | CCTCAGTCTG | CTCTGAAAAT | GAATCTGAAG | CTGAGGCCGA | CCAGCAAATG | 360 |
| GATAACTTGT | ACCTGAAAGC | CTTGGAGGGT | TTCATTGCTG | TGGTGACCCA | AGACGGTGAC | 420 |
| ATGATCTTTC | TGTCGGAAAA | CATCAGCAAG | TTCATGGGAC | TTACTCAGGT | AGAACTAACA | 480 |
| GGACACAGCA | TCTTTGACTT | CACTCATCCT | TGCGACCATG | AAGAGATCCG | TGAGAACCTG | 540 |
| ACTCTCAAAA | ACGGCTCTGG | TTTTGGGAAG | AAGAGCAAAG | ACGTGTCCAC | CGAGCGTGAC | 600 |
| TTCTTCATGA | GGATGAAGTG | CACGGTCACC | AACAGAGGCC | GGACTGTCAA | CCTCAAGTCG | 660 |
| GCCACCTGGA | AGTCCGTCCT | GCACTGCACC | GGGCAAGTGA | GAGTCTACAA | CAACTGCCCC | 720 |
| CCTCACAGTA | GCCTCTGTGG | CTCCAAGGAG | CCCCTGCTGT | CCTGCCTTAT | CATCATGTGT | 780 |
| GAGCCAATCC | AGCACCCATC | CCACATGGAC | ATCCCCTGG | ACAGCAAGAC | TTTCCTGAGC | 840 |
| CGCCACAGCA | TGGACATGAA | GTTCACCTAC | TGTGACGACA | GAATCTTGGA | ACTGATTGGT | 900 |
| TACCACCCCG | AGGAGCTACT | GGACGCTCT | GCCTATAGT | TTTACCATGC | CCTGGATTCG | 960 |
| GAGAACATGA | CCAAAAGTCA | CCAGAACTTG | TGCACCAAGG | GGCAGGTGGT | ATCTGGCCAG | 1020 |

-continued

```
TACCGGATGC TAGCCAAACA CGGAGGATAT GTGTGGCTGG AGACCCAGGG GACGGTCATC    1080
TACAACCCCC GCAACCTGCA GCCTCAGTGT ATCATGTGTG TCAACTATGT GCTGAGTGAG    1140
ATCGAGAAGA ACGACGTGGT GTTCTCCATG GACCAGACCG AATCCCTGTT CAAGCCACAC    1200
CTGATGGCCA TGAACAGCAT CTTTGACAGC AGTGACGATG TGGCTGTAAC TGAGAAGAGC    1260
AACTACCTGT TCACCAAACT GAAGGAGGAG CCCGAGGAAC TGGCCCAGTT GGCCCCACC     1320
CCAGGAGATG CCATTATTTC TCTCGATTTC GGAAGCCAGA ACTTCGATGA CCCTCAGCC     1380
TATGGCAAGG CCATCCTTCC CCCGGGCCAG CCATGGGTCT CGGGGCTGAG GAGCCACAGT    1440
GCCCAGAGCG AGTCCGGGAG CCTGCCAGCC TTCACTGTGC CCCAGGCAGA CACCCCAGGG    1500
AACACTACAC CCAGTGCTTC AAGCAGCAGT AGCTGCTCCA CGCCCAGCAG CCCTGAGGAC    1560
TACTATTCAT CCTTGGAGAA TCCCTTGAAG ATCGAAGTGA TTGAGAAGCT TTTCGCCATG    1620
GACACGGAGC CGAGGGACCC GGGCAGTACC CAGACGGACT TCAGTGAACT GGATTTGGAG    1680
ACCTTGGCAC CCTACATCCC TATGGACGGC GAGGACTTCC AGCTGAGCCC CATCTGCCCA    1740
GAGGAGCCGC TCATGCCAGA GAGCCCCCAG CCCACCCCCC AGCACTGCTT CAGTACCATG    1800
ACCAGCATCT TCCAGCCGCT CACCCCGGGG CCACCCACG GCCCCTTCTT CCTCGATAAG     1860
TACCCGCAGC AGTTGGAAAG CAGGAAGACA GAGTCTGAGC ACTGGCCCAT GTCTTCCATC    1920
TTCTTTGATG CTGGGAGCAA AGGGTCCCTG TCTCCATGCT GTGGCCAGGC CAGCACCCCT    1980
CTCTCTTCTA TGGGAGGCAG ATCCAACACG CAGTGGCCCC CGGATCCACC ATTACATTTC    2040
GGCCCTACTA AGTGGCCTGT GGGTGATCAG AGTGCTGAAT CCCTGGGAGC CCTGCCGGTG    2100
GGGTCATGGC AGTTGGAACT TCCGAGCGCC CCGCTTCATG TCTCCATGTT CAAGATGAGG    2160
TCTGCAAAGG ACTTCGGGGC CCGAGGTCCA TACATGATGA GCCCAGCCAT GATCGCCCTG    2220
TCCAACAAGC TGAAGCTAAA GCGGCAGCTG GAGTATGAGG AGCAAGCCTT CCAAGACACA    2280
AGCGGGGGGG ACCCTCCAGG CACCAGCAGT TCACACTTGA TGTGGAAACG TATGAAGAGC    2340
CTCATGGGCG GGACCTGTCC TTTGATGCCT GACAAGACCA TCAGTGCGAA CATGGCCCCC    2400
GATGAATTCA CCCAAAAATC TATGAGAGGC CTGGGCCAGC CACTGAGACA CCTGCCACCT    2460
CCCCAGCCAC CATCTACCAG GAGCTCAGGG GAGAACGCCA AGACTGGGTT CCCGCCACAG    2520
TGCTATGCCT CCCAGTTCCA GGACTACGGT CCTCCAGGAG CTCAAAAGGT GTCAGGCGTG    2580
GCCAGTCGAC TGCTGGGGCC ATCGTTCGAG CCTTACCTGT GCCGGAACT GACCAGATAT     2640
GACTGTGAGG TGAACGTGCC CGTGCCTGGA AGCTCCACAC TCCTGCAGGG GAGAGACCTT    2700
CTCAGAGCTC TGGACCAGGC CACCTGAGCC AGGGCCTCTG GCCGGGCATG CCCCTGCCTG    2760
CCCCGCCGTC TTGACCTGCC AGCTTCACTT CCATCTGTGT TGCTATTAGG TATCTCTAAC    2820
ACCAGCACAC TTCTTACGAG ATGTACTCAA CCTGGCCTAC TGGCCAGGTC ACCAAGCAGT    2880
GGCCTTTATC TGACATGCTC ACTTTATTAT CCATGTTTTA AAAATACATA GTTGTTGTAC    2940
CTGCTATGTT TTACCGTTGA TGAAAGTGTT CTGAAATTTT ATAAGATTTC CCCCTCCCTC    3000
CCTCCCTTGA ATTACTTCTA ATTTATATTC C                                  3031
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

GCCCTACGTG CTGTCTCA 18

( 2 ) INFORMATION FOR SEQ ID NO:4:

( i ) SEQUENCE CHARACTERISTICS:
        ( A ) LENGTH: 870 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met Thr Ala Asp Lys Glu Lys Lys Arg Ser Ser Ser Glu Arg Arg Lys
 1               5                  10                  15

Glu Lys Ser Arg Asp Ala Ala Arg Cys Arg Arg Ser Lys Glu Thr Glu
                20                  25                  30

Val Phe Tyr Glu Leu Ala His Glu Leu Pro Leu Pro His Ser Val Ser
            35                  40                  45

Ser His Leu Asp Lys Ala Ser Ile Met Arg Leu Glu Ile Ser Phe Leu
    50                  55                  60

Arg Thr His Lys Leu Leu Ser Ser Val Cys Ser Glu Asn Glu Ser Glu
65                  70                  75                  80

Ala Glu Ala Asp Gln Gln Met Asp Asn Leu Tyr Leu Lys Ala Leu Glu
                85                  90                  95

Gly Phe Ile Ala Val Val Thr Gln Asp Gly Asp Met Ile Phe Leu Ser
            100                 105                 110

Glu Asn Ile Ser Lys Phe Met Gly Leu Thr Gln Val Glu Leu Thr Gly
            115                 120                 125

His Ser Ile Phe Asp Phe Thr His Pro Cys Asp His Glu Glu Ile Arg
    130                 135                 140

Glu Asn Leu Ser Leu Lys Asn Gly Ser Gly Phe Gly Lys Lys Ser Lys
145                 150                 155                 160

Asp Met Ser Thr Glu Arg Asp Phe Phe Met Arg Met Lys Cys Thr Val
                165                 170                 175

Thr Asn Arg Gly Arg Thr Val Asn Leu Lys Ser Ala Thr Trp Lys Val
            180                 185                 190

Leu His Cys Thr Gly Gln Val Lys Val Tyr Asn Asn Cys Pro Pro His
        195                 200                 205

Asn Ser Leu Cys Gly Tyr Lys Glu Pro Leu Leu Ser Cys Leu Ile Ile
    210                 215                 220

Met Cys Glu Pro Ile Gln His Pro Ser His Met Asp Ile Pro Leu Asp
225                 230                 235                 240

Ser Lys Thr Phe Leu Ser Arg His Ser Met Asp Met Lys Phe Thr Tyr
                245                 250                 255

Cys Asp Asp Arg Ile Thr Glu Leu Ile Gly Tyr His Pro Glu Glu Leu
            260                 265                 270

Leu Gly Arg Ser Ala Tyr Glu Phe Tyr His Ala Leu Asp Ser Glu Asn
            275                 280                 285

Met Thr Lys Ser His Gln Asn Leu Cys Thr Lys Gly Gln Val Val Ser
    290                 295                 300

Gly Gln Tyr Arg Met Leu Ala Lys His Gly Gly Tyr Val Trp Leu Glu
305                 310                 315                 320

Thr Gln Gly Thr Val Ile Tyr Asn Pro Arg Asn Leu Gln Pro Gln Cys
                325                 330                 335
```

```
Ile Met Cys Val Asn Tyr Val Leu Ser Glu Ile Glu Lys Asn Asp Val
            340                 345                 350
Val Phe Ser Met Asp Gln Thr Glu Ser Leu Phe Lys Pro His Leu Met
        355                 360                 365
Ala Met Asn Ser Ile Phe Asp Ser Ser Gly Lys Gly Ala Val Ser Glu
    370                 375                 380
Lys Ser Asn Phe Leu Phe Thr Lys Leu Lys Glu Glu Pro Glu Glu Leu
385                 390                 395                 400
Ala Gln Leu Ala Pro Thr Pro Gly Asp Ala Ile Ile Ser Leu Asp Phe
                405                 410                 415
Gly Asn Gln Asn Phe Glu Glu Ser Ser Ala Tyr Gly Lys Ala Ile Leu
            420                 425                 430
Pro Pro Ser Gln Pro Trp Ala Thr Glu Leu Arg Ser His Ser Thr Gln
        435                 440                 445
Ser Glu Ala Gly Ser Leu Pro Ala Phe Thr Val Pro Gln Ala Ala Ala
    450                 455                 460
Pro Gly Ser Thr Thr Pro Ser Ala Thr Ser Ser Ser Ser Ser Cys Ser
465                 470                 475                 480
Thr Pro Asn Ser Pro Glu Asp Tyr Tyr Thr Ser Leu Asp Asn Asp Leu
                485                 490                 495
Lys Ile Glu Val Ile Glu Lys Leu Phe Ala Met Asp Thr Glu Ala Lys
            500                 505                 510
Asp Gln Cys Ser Thr Gln Thr Asp Phe Asn Glu Leu Asp Leu Glu Thr
        515                 520                 525
Leu Ala Pro Tyr Ile Pro Met Asp Gly Glu Asp Phe Gln Leu Ser Pro
    530                 535                 540
Ile Cys Pro Glu Glu Arg Leu Leu Ala Glu Asn Pro Gln Ser Thr Pro
545                 550                 555                 560
Gln His Cys Phe Ser Ala Met Thr Asn Ile Phe Gln Pro Leu Ala Pro
                565                 570                 575
Val Ala Pro His Ser Pro Phe Leu Leu Asp Lys Phe Gln Gln Gln Leu
            580                 585                 590
Glu Ser Lys Lys Thr Glu Pro Glu His Arg Pro Met Ser Ser Ile Phe
        595                 600                 605
Phe Asp Ala Gly Ser Lys Ala Ser Leu Pro Pro Cys Cys Gly Gln Ala
    610                 615                 620
Ser Thr Pro Leu Ser Ser Met Gly Gly Arg Ser Asn Thr Gln Trp Pro
625                 630                 635                 640
Pro Asp Pro Pro Leu His Phe Gly Pro Thr Lys Trp Ala Val Gly Asp
                645                 650                 655
Gln Arg Thr Glu Phe Leu Gly Ala Ala Pro Leu Gly Pro Pro Val Ser
            660                 665                 670
Pro Pro His Val Ser Thr Phe Lys Thr Arg Ser Ala Lys Gly Phe Gly
        675                 680                 685
Ala Arg Gly Pro Asp Val Leu Ser Pro Ala Met Val Ala Leu Ser Asn
    690                 695                 700
Lys Leu Lys Leu Lys Arg Gln Leu Glu Tyr Glu Glu Gln Ala Phe Gln
705                 710                 715                 720
Asp Leu Ser Gly Gly Asp Pro Pro Gly Gly Ser Thr Ser His Leu Met
                725                 730                 735
Trp Lys Arg Met Lys Asn Leu Arg Gly Gly Ser Cys Pro Leu Met Pro
            740                 745                 750
Asp Lys Pro Leu Ser Ala Asn Val Pro Asn Asp Lys Phe Thr Gln Asn
        755                 760                 765
```

```
Pro  Met  Arg  Gly  Leu  Gly  His  Pro  Leu  Arg  His  Leu  Pro  Leu  Pro  Gln
     770            775                      780

Pro  Pro  Ser  Ala  Ile  Ser  Pro  Gly  Glu  Asn  Ser  Lys  Ser  Arg  Phe  Pro
785                      790                 795                           800

Pro  Gln  Cys  Tyr  Ala  Thr  Gln  Tyr  Gln  Asp  Tyr  Ser  Leu  Ser  Ser  Ala
                    805                 810                      815

His  Lys  Val  Ser  Gly  Met  Ala  Ser  Arg  Leu  Leu  Gly  Pro  Ser  Phe  Glu
               820                 825                      830

Ser  Tyr  Leu  Leu  Pro  Glu  Leu  Thr  Arg  Tyr  Asp  Cys  Glu  Val  Asn  Val
835                           840                      845

Pro  Val  Leu  Gly  Ser  Ser  Thr  Leu  Leu  Gln  Gly  Gly  Asp  Leu  Leu  Arg
     850                 855                      860

Ala  Leu  Asp  Gln  Ala  Thr
865                      870
```

(2) INFORMATION FOR SEQ ID NO:5:

(i) SEQUENCE CHARACTERISTICS:
        (A) LENGTH: 875 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met  Thr  Ala  Asp  Lys  Glu  Lys  Lys  Arg  Ser  Ser  Ser  Glu  Leu  Arg  Lys
1                   5                   10                      15

Glu  Lys  Ser  Arg  Asp  Ala  Ala  Arg  Cys  Arg  Arg  Ser  Lys  Glu  Thr  Glu
               20                  25                      30

Val  Phe  Tyr  Glu  Leu  Ala  His  Glu  Leu  Pro  Leu  Pro  His  Ser  Val  Ser
          35                      40                      45

Ser  His  Leu  Asp  Lys  Ala  Ser  Ile  Met  Arg  Leu  Ala  Ile  Ser  Phe  Leu
     50                  55                      60

Arg  Thr  His  Lys  Leu  Leu  Ser  Ser  Val  Cys  Ser  Glu  Asn  Glu  Ser  Glu
65                       70                      75                      80

Ala  Glu  Ala  Asp  Gln  Gln  Met  Asp  Asn  Leu  Tyr  Leu  Lys  Ala  Leu  Glu
               85                       90                      95

Gly  Phe  Ile  Ala  Val  Val  Thr  Gln  Asp  Gly  Asp  Met  Ile  Phe  Leu  Ser
               100                      105                     110

Glu  Asn  Ile  Ser  Lys  Phe  Met  Gly  Leu  Thr  Gln  Val  Glu  Leu  Thr  Gly
          115                      120                     125

His  Ser  Ile  Phe  Asp  Phe  Thr  His  Pro  Cys  Asp  His  Glu  Glu  Ile  Arg
     130                      135                     140

Glu  Asn  Leu  Thr  Leu  Lys  Asn  Gly  Ser  Gly  Phe  Gly  Lys  Lys  Ser  Lys
145                 150                      155                          160

Asp  Val  Ser  Thr  Glu  Arg  Asp  Phe  Phe  Met  Arg  Met  Lys  Cys  Thr  Val
               165                      170                     175

Thr  Asn  Arg  Gly  Arg  Thr  Val  Asn  Leu  Lys  Ser  Ala  Thr  Trp  Lys  Ser
               180                      185                     190

Val  Leu  His  Cys  Thr  Gly  Gln  Val  Arg  Val  Tyr  Asn  Asn  Cys  Pro  Pro
          195                      200                     205

His  Ser  Ser  Leu  Cys  Gly  Ser  Lys  Glu  Pro  Leu  Leu  Ser  Cys  Leu  Ile
     210                      215                     220

Ile  Met  Cys  Glu  Pro  Ile  Gln  His  Pro  Ser  His  Met  Asp  Ile  Pro  Leu
225                      230                     235                          240
```

Asp Ser Lys Thr Phe Leu Ser Arg His Ser Met Asp Met Lys Phe Thr
                245                 250                 255

Tyr Cys Asp Asp Arg Ile Leu Glu Leu Ile Gly Tyr His Pro Glu Glu
            260                 265                 270

Leu Leu Gly Arg Ser Ala Tyr Glu Phe Tyr His Ala Leu Asp Ser Glu
            275                 280                 285

Asn Met Thr Lys Ser His Gln Asn Leu Cys Thr Lys Gly Gln Val Val
    290                 295                 300

Ser Gly Gln Tyr Arg Met Leu Ala Lys His Gly Gly Tyr Val Trp Leu
305                 310                 315                 320

Glu Thr Gln Gly Thr Val Ile Tyr Asn Pro Arg Asn Leu Gln Pro Gln
                325                 330                 335

Cys Ile Met Cys Val Asn Tyr Val Leu Ser Glu Ile Glu Lys Asn Asp
            340                 345                 350

Val Val Phe Ser Met Asp Gln Thr Glu Ser Leu Phe Lys Pro His Leu
            355                 360                 365

Met Ala Met Asn Ser Ile Phe Asp Ser Ser Asp Val Ala Val Thr
    370                 375                 380

Glu Lys Ser Asn Tyr Leu Phe Thr Lys Leu Lys Glu Glu Pro Glu Glu
385                 390                 395                 400

Leu Ala Gln Leu Ala Pro Thr Pro Gly Asp Ala Ile Ile Ser Leu Asp
            405                 410                 415

Phe Gly Ser Gln Asn Phe Asp Glu Pro Ser Ala Tyr Gly Lys Ala Ile
            420                 425                 430

Leu Pro Pro Gly Gln Pro Trp Val Ser Gly Leu Arg Ser His Ser Ala
            435                 440                 445

Gln Ser Glu Ser Gly Ser Leu Pro Ala Phe Thr Val Pro Gln Ala Asp
    450                 455                 460

Thr Pro Gly Asn Thr Thr Pro Ser Ala Ser Ser Ser Ser Ser Cys Ser
465                 470                 475                 480

Thr Pro Ser Ser Pro Glu Asp Tyr Tyr Ser Ser Leu Glu Asn Pro Leu
            485                 490                 495

Lys Ile Glu Val Ile Glu Lys Leu Phe Ala Met Asp Thr Glu Pro Arg
            500                 505                 510

Asp Pro Gly Ser Thr Gln Thr Asp Phe Ser Glu Leu Asp Leu Glu Thr
            515                 520                 525

Leu Ala Pro Tyr Ile Pro Met Asp Gly Glu Asp Phe Gln Leu Ser Pro
    530                 535                 540

Ile Cys Pro Glu Glu Pro Leu Met Pro Glu Ser Pro Gln Pro Thr Pro
545                 550                 555                 560

Gln His Cys Phe Ser Thr Met Thr Ser Ile Phe Gln Pro Leu Thr Pro
            565                 570                 575

Gly Ala Thr His Gly Pro Phe Phe Leu Asp Lys Tyr Pro Gln Gln Leu
            580                 585                 590

Glu Ser Arg Lys Thr Glu Ser Glu His Trp Pro Met Ser Ser Ile Phe
            595                 600                 605

Phe Asp Ala Gly Ser Lys Gly Ser Leu Ser Pro Cys Cys Gly Gln Ala
    610                 615                 620

Ser Thr Pro Leu Ser Ser Met Gly Gly Arg Ser Asn Thr Gln Trp Pro
625                 630                 635                 640

Pro Asp Pro Pro Leu His Phe Gly Pro Thr Lys Trp Pro Val Gly Asp
            645                 650                 655

Gln Ser Ala Glu Ser Leu Gly Ala Leu Pro Val Gly Ser Trp Gln Leu
            660                 665                 670

```
Glu  Leu  Pro  Ser  Ala  Pro  Leu  His  Val  Ser  Met  Phe  Lys  Met  Arg  Ser
          675                      680                     685

Ala  Lys  Asp  Phe  Gly  Ala  Arg  Gly  Pro  Tyr  Met  Met  Ser  Pro  Ala  Met
     690                 695                     700

Ile  Ala  Leu  Ser  Asn  Lys  Leu  Lys  Leu  Lys  Arg  Gln  Leu  Glu  Tyr  Glu
705                      710                     715                          720

Glu  Gln  Ala  Phe  Gln  Asp  Thr  Ser  Gly  Gly  Asp  Pro  Pro  Gly  Thr  Ser
                    725                      730                     735

Ser  Ser  His  Leu  Met  Trp  Lys  Arg  Met  Lys  Ser  Leu  Met  Gly  Gly  Thr
               740                      745                     750

Cys  Pro  Leu  Met  Pro  Asp  Lys  Thr  Ile  Ser  Ala  Asn  Met  Ala  Pro  Asp
          755                      760                     765

Glu  Phe  Thr  Gln  Lys  Ser  Met  Arg  Gly  Leu  Gly  Gln  Pro  Leu  Arg  His
     770                      775                     780

Leu  Pro  Pro  Pro  Gln  Pro  Pro  Ser  Thr  Arg  Ser  Ser  Gly  Glu  Asn  Ala
785                      790                     795                          800

Lys  Thr  Gly  Phe  Pro  Pro  Gln  Cys  Tyr  Ala  Ser  Gln  Phe  Gln  Asp  Tyr
                    805                      810                     815

Gly  Pro  Pro  Gly  Ala  Gln  Lys  Val  Ser  Gly  Val  Ala  Ser  Arg  Leu  Leu
               820                      825                     830

Gly  Pro  Ser  Phe  Glu  Pro  Tyr  Leu  Leu  Pro  Glu  Leu  Thr  Arg  Tyr  Asp
          835                      840                     845

Cys  Glu  Val  Asn  Val  Pro  Val  Pro  Gly  Ser  Ser  Thr  Leu  Leu  Gln  Gly
     850                      855                     860

Arg  Asp  Leu  Leu  Arg  Ala  Leu  Asp  Gln  Ala  Thr
865                      870                     875
```

( 2 ) INFORMATION FOR SEQ ID NO:6:

( i ) SEQUENCE CHARACTERISTICS:
        ( A ) LENGTH: 826 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Met  Glu  Gly  Ala  Gly  Gly  Ala  Asn  Asp  Lys  Lys  Lys  Ile  Ser  Ser  Glu
1                   5                    10                      15

Arg  Arg  Lys  Glu  Lys  Ser  Arg  Asp  Ala  Arg  Ser  Arg  Ser  Lys
               20                   25                   30

Glu  Ser  Glu  Val  Phe  Tyr  Glu  Leu  Ala  His  Gln  Leu  Pro  Leu  Pro  His
          35                      40                     45

Asn  Val  Ser  Ser  His  Leu  Asp  Lys  Ala  Ser  Val  Met  Arg  Leu  Thr  Ile
     50                      55                     60

Ser  Tyr  Leu  Arg  Val  Arg  Lys  Leu  Leu  Asp  Ala  Gly  Asp  Leu  Asp  Ile
65                       70                     75                           80

Glu  Asp  Asp  Met  Lys  Ala  Gln  Met  Asn  Cys  Phe  Tyr  Leu  Lys  Ala  Leu
                    85                      90                      95

Asp  Gly  Phe  Val  Met  Val  Leu  Thr  Asp  Asp  Gly  Asp  Met  Ile  Tyr  Ile
               100                      105                    110

Ser  Asp  Asn  Val  Asn  Lys  Tyr  Met  Gly  Leu  Thr  Gln  Phe  Glu  Leu  Thr
          115                      120                    125

Gly  His  Ser  Val  Phe  Asp  Phe  Thr  His  Pro  Cys  Asp  His  Glu  Glu  Met
     130                      135                    140
```

```
Arg  Glu  Met  Leu  Thr  His  Arg  Asn  Gly  Leu  Val  Lys  Lys  Gly  Lys  Glu
145                      150                      155                      160

Gln  Asn  Thr  Gln  Arg  Ser  Phe  Phe  Leu  Arg  Met  Lys  Cys  Thr  Leu  Thr
                    165                      170                      175

Ser  Arg  Gly  Arg  Thr  Met  Asn  Ile  Lys  Ser  Ala  Thr  Trp  Lys  Val  Leu
               180                      185                      190

His  Cys  Thr  Gly  His  Ile  His  Val  Tyr  Asp  Thr  Asn  Ser  Asn  Gln  Pro
          195                      200                      205

Gln  Cys  Gly  Tyr  Lys  Lys  Pro  Pro  Met  Thr  Cys  Leu  Val  Leu  Ile  Cys
     210                      215                      220

Glu  Pro  Ile  Pro  His  Pro  Ser  Asn  Ile  Glu  Ile  Pro  Leu  Asp  Ser  Lys
225                      230                      235                      240

Thr  Phe  Leu  Ser  Arg  His  Ser  Leu  Asp  Met  Lys  Phe  Ser  Tyr  Cys  Asp
                    245                      250                      255

Glu  Arg  Ile  Thr  Glu  Leu  Met  Gly  Tyr  Glu  Pro  Glu  Glu  Leu  Leu  Gly
               260                      265                      270

Arg  Ser  Ile  Tyr  Glu  Tyr  Tyr  His  Ala  Leu  Asp  Ser  Asp  His  Leu  Thr
          275                      280                      285

Lys  Thr  His  His  Asp  Met  Phe  Thr  Lys  Gly  Gln  Val  Thr  Thr  Gly  Gln
     290                      295                      300

Tyr  Arg  Met  Leu  Ala  Lys  Arg  Gly  Gly  Tyr  Val  Trp  Val  Glu  Thr  Gln
305                      310                      315                      320

Ala  Thr  Val  Ile  Tyr  Asn  Thr  Lys  Asn  Ser  Gln  Pro  Gln  Cys  Ile  Val
                    325                      330                      335

Cys  Val  Asn  Tyr  Val  Val  Ser  Gly  Ile  Ile  Gln  His  Asp  Leu  Ile  Phe
               340                      345                      350

Ser  Leu  Gln  Gln  Thr  Glu  Cys  Val  Leu  Lys  Pro  Val  Glu  Ser  Ser  Asp
          355                      360                      365

Met  Lys  Met  Thr  Gln  Leu  Phe  Thr  Lys  Val  Glu  Ser  Glu  Asp  Thr  Ser
     370                      375                      380

Ser  Leu  Phe  Asp  Lys  Leu  Lys  Lys  Glu  Pro  Asp  Ala  Leu  Thr  Leu  Leu
385                      390                      395                      400

Ala  Pro  Ala  Ala  Gly  Asp  Thr  Ile  Ile  Ser  Leu  Asp  Phe  Gly  Ser  Asn
                    405                      410                      415

Asp  Thr  Glu  Thr  Asp  Asp  Gln  Gln  Leu  Glu  Glu  Val  Pro  Leu  Tyr  Asn
               420                      425                      430

Asp  Val  Met  Leu  Pro  Ser  Pro  Asn  Glu  Lys  Leu  Gln  Asn  Ile  Asn  Leu
          435                      440                      445

Ala  Met  Ser  Pro  Leu  Pro  Thr  Ala  Glu  Thr  Pro  Lys  Pro  Leu  Arg  Ser
     450                      455                      460

Ser  Ala  Asp  Pro  Ala  Leu  Asn  Gln  Glu  Val  Ala  Leu  Lys  Leu  Glu  Pro
465                      470                      475                      480

Asn  Pro  Glu  Ser  Leu  Glu  Leu  Ser  Phe  Thr  Met  Pro  Gln  Ile  Gln  Asp
                    485                      490                      495

Gln  Thr  Pro  Ser  Pro  Ser  Asp  Gly  Ser  Thr  Arg  Gln  Ser  Ser  Pro  Glu
               500                      505                      510

Pro  Asn  Ser  Pro  Ser  Glu  Tyr  Cys  Phe  Tyr  Val  Asp  Ser  Asp  Met  Val
          515                      520                      525

Asn  Glu  Phe  Lys  Leu  Glu  Leu  Val  Glu  Lys  Leu  Phe  Ala  Glu  Asp  Thr
     530                      535                      540

Glu  Ala  Lys  Asn  Pro  Phe  Ser  Thr  Gln  Asp  Thr  Asp  Leu  Asp  Leu  Glu
545                      550                      555                      560

Met  Leu  Ala  Pro  Tyr  Ile  Pro  Met  Asp  Asp  Asp  Phe  Gln  Leu  Arg  Ser
                    565                      570                      575
```

```
Phe Asp Gln Leu Ser Pro Leu Glu Ser Ser Ser Ala Ser Pro Glu Ser
             580                 585                 590

Ala Ser Pro Gln Ser Thr Val Thr Val Phe Gln Gln Thr Gln Ile Gln
         595                 600                 605

Glu Pro Thr Ala Asn Ala Thr Thr Thr Thr Ala Thr Thr Asp Glu Leu
     610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
             645                 650                 655

Ser Pro Tyr Arg Asp Thr Gln Ser Arg Thr Ala Ser Pro Asn Arg Ala
             660                 665                 670

Gly Lys Gly Val Ile Glu Gln Thr Glu Lys Ser His Pro Arg Ser Pro
         675                 680                 685

Asn Val Leu Ser Val Ala Leu Ser Gln Arg Thr Thr Val Pro Glu Glu
     690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
             725                 730                 735

Leu Leu Gln Gln Pro Asp Asp His Ala Ala Thr Thr Ser Leu Ser Trp
             740                 745                 750

Lys Arg Val Lys Gly Cys Lys Ser Ser Glu Gln Asn Gly Met Glu Gln
         755                 760                 765

Lys Thr Ile Ile Leu Ile Pro Ser Asp Leu Ala Cys Arg Leu Leu Gly
     770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
             805                 810                 815

Glu Leu Leu Arg Ala Leu Asp Gln Val Asn
             820                 825
```

(2) INFORMATION FOR SEQ ID NO:7:

(i) SEQUENCE CHARACTERISTICS:
      (A) LENGTH: 810 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:7:

```
Met Ser Ser Glu Arg Arg Lys Glu Lys Ser Arg Asp Ala Ala Arg Ser
1               5                   10                  15

Arg Arg Thr Lys Glu Ser Glu Val Phe Tyr Glu Leu Ala His Gln Leu
         20                  25                  30

Pro Leu Pro His Asn Val Ser Ser His Leu Asp Lys Ala Ser Val Met
     35                  40                  45

Arg Leu Thr Ile Ser Tyr Leu Arg Val Arg Lys Leu Leu Asp Ala Gly
     50                  55                  60

Gly Leu Asp Ser Glu Asp Glu Met Lys Ala Gln Met Asp Cys Phe Tyr
65              70                  75                  80

Leu Lys Ala Leu Asp Gly Phe Val Met Val Leu Thr Asp Asp Gly Asp
             85                  90                  95
```

```
Met Val Tyr Ile Ser Asp Asn Val Asn Lys Tyr Met Gly Leu Thr Gln
            100                 105                 110
Phe Glu Leu Ala Gly His Ser Val Phe Asp Phe Thr His Pro Cys Asp
        115                 120                 125
His Glu Glu Met Arg Glu Met Leu Thr His Arg Asn Gly Pro Val Arg
    130                 135                 140
Lys Gly Lys Glu Leu Asn Thr Gln Arg Ser Phe Phe Leu Arg Met Lys
145                 150                 155                 160
Cys Thr Leu Thr Ser Arg Gly Arg Thr Met Asn Ile Lys Ser Ala Thr
                165                 170                 175
Trp Lys Val Leu His Cys Thr Gly His Ile His Val Tyr Asp Thr Asn
            180                 185                 190
Ser Asn Gln Pro Gln Cys Gly Tyr Lys Lys Pro Pro Met Thr Cys Leu
        195                 200                 205
Val Leu Ile Cys Glu Pro Ile Pro His Pro Ser Asn Ile Glu Ile Pro
    210                 215                 220
Leu Asp Ser Lys Thr Phe Leu Ser Arg His Ser Leu Asp Met Lys Phe
225                 230                 235                 240
Ser Tyr Cys Asp Glu Arg Ile Thr Glu Leu Met Gly Tyr Glu Pro Glu
                245                 250                 255
Glu Leu Leu Gly Arg Ser Ile Tyr Glu Tyr Tyr His Ala Leu Asp Ser
            260                 265                 270
Asp His Leu Thr Lys Thr His His Asp Met Phe Thr Lys Gly Gln Val
        275                 280                 285
Thr Thr Gly Gln Tyr Arg Met Leu Ala Lys Arg Gly Gly Tyr Val Trp
    290                 295                 300
Val Glu Thr Gln Ala Thr Val Ile Tyr Asn Thr Lys Asn Ser Gln Pro
305                 310                 315                 320
Gln Cys Ile Val Cys Val Asn Tyr Val Val Ser Gly Ile Ile Gln His
                325                 330                 335
Asp Leu Ile Phe Ser Leu Gln Gln Thr Glu Ser Val Leu Lys Pro Val
            340                 345                 350
Glu Ser Ser Asp Met Lys Met Thr Gln Leu Phe Thr Lys Val Glu Ser
        355                 360                 365
Glu Asp Thr Ser Cys Leu Phe Asp Lys Leu Lys Lys Glu Pro Asp Ala
    370                 375                 380
Leu Thr Leu Leu Ala Pro Ala Ala Gly Asp Thr Ile Ile Ser Leu Asp
385                 390                 395                 400
Phe Gly Ser Asp Asp Thr Glu Thr Glu Asp Gln Gln Leu Glu Asp Val
                405                 410                 415
Pro Leu Tyr Asn Asp Val Met Phe Pro Ser Ser Asn Glu Lys Leu Asn
            420                 425                 430
Ile Asn Leu Ala Met Ser Pro Leu Pro Ser Ser Glu Thr Pro Lys Pro
        435                 440                 445
Leu Arg Ser Ser Ala Asp Pro Ala Leu Asn Gln Glu Val Ala Leu Lys
    450                 455                 460
Leu Glu Ser Ser Pro Glu Ser Leu Gly Leu Ser Phe Thr Met Pro Gln
465                 470                 475                 480
Ile Gln Asp Gln Pro Ala Ser Pro Ser Asp Gly Ser Thr Arg Gln Ser
                485                 490                 495
Ser Pro Glu Pro Asn Ser Pro Ser Glu Tyr Cys Phe Asp Val Asp Ser
            500                 505                 510
Asp Met Val Asn Val Phe Lys Leu Glu Leu Val Glu Lys Leu Phe Ala
        515                 520                 525
```

```
Glu Asp Thr Glu Ala Lys Asn Pro Phe Ser Thr Gln Asp Thr Asp Leu
    530                 535                 540
Asp Leu Glu Met Leu Ala Pro Tyr Ile Pro Met Asp Asp Asp Phe Gln
545                 550                 555                 560
Leu Arg Ser Phe Asp Gln Leu Ser Pro Leu Glu Ser Asn Ser Pro Ser
                565                 570                 575
Pro Pro Ser Met Ser Thr Val Thr Gly Phe Gln Gln Thr Gln Leu Gln
            580                 585                 590
Lys Pro Thr Ile Thr Ala Thr Ala Thr Thr Thr Ala Thr Thr Asp Glu
        595                 600                 605
Ser Lys Thr Glu Thr Lys Asp Asn Lys Glu Asp Ile Lys Ile Leu Ile
    610                 615                 620
Ala Ser Pro Ser Ser Thr Gln Val Pro Gln Glu Thr Thr Thr Ala Lys
625                 630                 635                 640
Ala Ser Ala Tyr Ser Gly Thr His Ser Arg Thr Ala Ser Pro Asp Arg
                645                 650                 655
Ala Gly Lys Arg Val Ile Glu Gln Thr Asp Lys Ala His Pro Arg Ser
            660                 665                 670
Leu Asn Leu Ser Ala Thr Leu Asn Gln Arg Asn Thr Val Pro Glu Glu
        675                 680                 685
Glu Leu Asn Pro Lys Thr Ile Ala Ser Gln Asn Ala Gln Arg Lys Arg
    690                 695                 700
Lys Met Glu His Asp Gly Ser Leu Phe Gln Ala Ala Gly Ile Gly Thr
705                 710                 715                 720
Leu Leu Gln Gln Pro Gly Asp Cys Ala Pro Thr Met Ser Leu Ser Trp
                725                 730                 735
Lys Arg Val Lys Gly Phe Ile Ser Ser Glu Gln Asn Gly Thr Glu Gln
            740                 745                 750
Lys Thr Ile Ile Leu Ile Pro Ser Asp Leu Ala Cys Arg Leu Leu Gly
        755                 760                 765
Gln Ser Met Asp Val Ser Gly Leu Pro Gln Leu Thr Ser Tyr Asp Cys
    770                 775                 780
Glu Val Asn Ala Pro Ile Gln Gly Ser Arg Asn Leu Leu Gln Gly Glu
785                 790                 795                 800
Glu Leu Leu Arg Ala Leu Asp Gln Val Asn
                805                 810
```